(12) United States Patent
Hauer et al.

(10) Patent No.: US 8,509,898 B2
(45) Date of Patent: Aug. 13, 2013

(54) ELECTRONIC DEVICE OR ELECTRIC COMPONENT

(75) Inventors: Marc Hauer, Zurich (CH); Stefan Eck, Hoechstadt (DE)

(73) Assignee: Dyconex AG, Bassersdorf (CH)

( * ) Notice: Subject to any disclaimer, the term of this patent is extended or adjusted under 35 U.S.C. 154(b) by 19 days.

(21) Appl. No.: 13/107,517

(22) Filed: May 13, 2011

(65) Prior Publication Data

US 2011/0288608 A1    Nov. 24, 2011

Related U.S. Application Data

(60) Provisional application No. 61/346,925, filed on May 21, 2010.

(51) Int. Cl.
*A61N 1/00* (2006.01)

(52) U.S. Cl.
USPC .......................................................... 607/36

(58) Field of Classification Search
USPC .................................... 607/36, 115, 119, 218
See application file for complete search history.

(56) References Cited

U.S. PATENT DOCUMENTS

| 4,804,336 | A  | * | 2/1989 | Miller et al. .................. 439/218 |
| 2005/0040513 | A1 |   | 2/2005 | Salmon |
| 2007/0182364 | A1 |   | 8/2007 | Zhao et al. |
| 2008/0312725 | A1 | * | 12/2008 | Penner .......................... 607/119 |
| 2010/0010560 | A1 | * | 1/2010 | Taylor et al. .................... 607/36 |
| 2010/0114205 | A1 | * | 5/2010 | Donofrio et al. ................. 607/4 |
| 2012/0203314 | A1 | * | 8/2012 | Deininger et al. ............ 607/115 |

FOREIGN PATENT DOCUMENTS

| EP | 0776016 | 5/1997 |
| WO | 2009086435 | 7/2009 |

OTHER PUBLICATIONS

European Search Report and Notes to the European Search Report on European Patent Application No. EP 11 16 5634, dated Aug. 25, 2011 (8 pages).

* cited by examiner

*Primary Examiner* — George Manuel
*Assistant Examiner* — Robert N Wieland
(74) *Attorney, Agent, or Firm* — Buchanan Ingersoll & Rooney PC

(57) ABSTRACT

An electronic device, comprising a housing, a functional unit disposed in the housing, a terminal lead electrically connecting the functional unit to the outside of the housing, and a sealed feedthrough in the housing, the feedthrough surrounding the terminal lead and insulating it with respect to the housing, wherein the feedthrough is produced from a liquid crystal polymer.

20 Claims, 4 Drawing Sheets

ELECTRONIC DEVICE OR ELECTRIC COMPONENT

CROSS-REFERENCE TO RELATED APPLICATIONS

This patent application claims the benefit U.S. Provisional Patent Application No. 61/346,925, filed on May 21, 2010, which is hereby incorporated by reference in its entirety.

TECHNICAL FIELD

The present invention relates generally to an electronic device or an electrical component, including a housing, a functional unit disposed in the housing, a terminal lead electrically connecting the functional unit to the outside of the housing, and a sealed feedthrough in the housing, the feedthrough surrounding the terminal lead and insulating it with respect to the housing.

BACKGROUND

In electronic devices and electrical components which must satisfy special requirements with respect to lasting sealing properties, the so-called feedthroughs around a terminal lead are especially critical regions. As a result, the design thereof has been the focus of special attention for years in devices such as implantable medical electronic devices (e.g., pacemakers, implantable cardioverters, cochlear implants, implantable neurostimulators, and the like). Producing the feedthrough from suitable ceramics, specifically surrounded by a metallic flange of the housing, has become established technology.

Specifically, for electrochemical components, such as, for example, batteries or electrolytic capacitors, a feedthrough is known from International Publication No. WO 2005/001997 A2, wherein a guide element made of a polymer is provided for receiving the terminal lead. From U.S. Publication No. 2007/0225771, a feedthrough assembly is known, which is used, for example, in a power source encasement of an implantable medical device and, in which, between the terminal lead and a ceramic or glass ring (forming the largest part of the feedthrough in terms of volume) a thin sleeve is provided, which is used, among other things, for compensating for the tolerances in the thermally highly sensitive metal-ceramic structure of the feedthrough. The thin sleeve can, in particular, be made of stainless steel, aluminum or titanium.

From U.S. Pat. No. 5,825,608, a feedthrough of an electronic device is known, which at the same time acts as a filter capacitor and can be used, for example, in implantable devices, such as pacemakers. In this feedthrough, a conductive polymer resin is used to establish electrical connections in a feedthrough body, which otherwise is substantially made of ceramics.

However, problems with respect to production tolerances and thermal loads are present when using conventional "hard" insulating materials, such as ceramics.

The present invention is directed at overcoming one or more of the above-identified problems.

SUMMARY

It is an object of the present invention to provide an improved electronic device or electrical component which, in particular, can be produced having high yield, is not sensitive to thermal loads, and/or enables reliable long-term operation.

According to a first aspect of the present invention, this object is achieved by an electronic device having the characteristics set forth in the respective independent claim(s) and, according to a second aspect of the present invention, it is achieved by an electrical component having the characteristics set forth in the respective independent claim(s). Advantageous refinements of the present inventive are the subject matter of the dependent claims.

In both aspects, the present invention encompasses producing the insulating regions of a feedthrough of the device or component, or in any case a significant section thereof, from a liquid crystal polymer. In this way, in particular the known problems regarding production tolerances and thermal loads can be prevented, which were typically observed with known metal-glass or metal-ceramic feedthrough designs. Even the use of the liquid crystal polymer ("LCP") in only a portion of the radial or lateral extension of the feedthrough, which is to say ultimately in combination with a conventional "hard" insulating material, allows significantly lower requirements with respect to the tolerances of the parts to be connected to each other in the feedthrough section during production and offers greater buffers regarding the reliability under thermal (alternating) loads.

In one embodiment of the present invention, the device is configured as an implantable medical electronic device. More specifically, the device is configured as a cardiac stimulator device and, in particular, as a pacemaker or cardioverter. However, other implantable medical devices are also contemplated.

In a further embodiment of the present invention, the feedthrough is made substantially solely from the liquid crystal polymer, in which particular metallic elements may be incorporated and/or applied. In an alternative embodiment to this, as already noted above, the liquid crystal polymer can be used in combination with a conventional insulating material, such as, for example, glass and/or ceramic, for producing only partial regions of the feedthrough. Specifically, such partial regions can be a surrounding region of the terminal lead and/or an edge region of the feedthrough, which, for example, specifically is in contact with a metal flange of the housing.

In light of the less favorable diffusion behavior of liquid crystal polymers compared to that of ceramics, further embodiments in which the diffusion cross-section is largely minimized and/or the diffusion length is largely maximized are advantageous. In this respect, a further embodiment that is advantageous is one in which the feedthrough includes alternating metal layers which start at the circumference and a center region, and do not fully extend to the center or the circumference, and which are disposed on the faces of the feedthrough and/or embedded in the liquid crystal polymer inside the feedthrough and form a labyrinth structure in the longitudinal section. As an alternative, it may be provided that the feedthrough includes a metal layer extending in a spiral shape from close to the upper face to close to the lower face. Other design embodiments serving the goal of a reduced diffusion cross-section and/or an increased diffusion length should also be regarded as advantageous.

According to a further embodiment of the present invention, at least one metal layer, in particular, a plurality of metal layers of a labyrinth structure, are rigidly connected to the terminal lead and/or integral therewith.

The electrical component according to the second aspect of the present invention is, in particular, configured as a capacitor or as a transmission unit and/or assembly of a message transmission or filtration system. Other components in which an extremely tightly sealed and thermally stable feedthrough is important can advantageously have the proposed structure as well.

In addition, the feedthrough of the electrical component can be configured in the same manner as the electronic device according to the first aspect of the invention. The feedthrough can, at the same time, be used to implement additional electrical functions, specifically in the above design configurations in which the LCP is combined with metallic elements (specifically layers).

In particular, the metallic elements, together with sections of the liquid crystal polymer, can form a capacitor which is arranged and connected to the functional unit of the device such that in this way an electrical function, in particular, a filtration or frequency-selective shielding function of the device is implemented. For example, the structure of the feedthrough including alternating LCP and metal layers mentioned above enables not only the capacitor and filter functions above-mentioned, but additional electrical/electronic functions, specifically in conjunction with a "daughterboard", which is combined with the feedthrough, for example, by a flexible connection and located directly in the region of the housing opening. When suitably dimensioned, in this way in particular, outer high frequency ("HF") interference fields can be shielded and the immunity to electromagnetic interference ("EMI") or the electromagnetic compatibility ("EMC") of a particular device can be increased.

For certain applications, a hybrid structure of the feedthrough can be useful in that a glass/$SiO_2$ passivation is applied on the side located outside the housing during use onto a main body having a liquid crystal polymer. For this purpose, long-term stable, biocompatible and corrosion-resistant glass is commercially available. Glass used in this way can additionally be provided with a thin $Al_2O_3$ cap soldered to the glass. With these measures, in particular, further improvements can be achieved with respect to the $H_2$ adsorption or $H_2$ absorption.

The connection of the proposed feedthrough to the wall of a metal housing, specifically a Ti housing, should be designed such that welding into the housing is possible—which necessitates the selection of a suitable material and geometry and, optionally, the provision of a welding screen—or the feedthrough is inserted in a housing part (a half shell) directly by gluing or soldering, in particular, before the housing is assembled.

Various other objects, aspects and advantages of the present invention can be obtained from a study of the specification, the drawings, and the appended claims.

DESCRIPTION OF THE DRAWINGS

Advantages and functional characteristics of the invention will additionally become apparent hereinafter from the description of two exemplary embodiments based on the figures. Shown are.

DETAILED DESCRIPTION

Figure 1A:
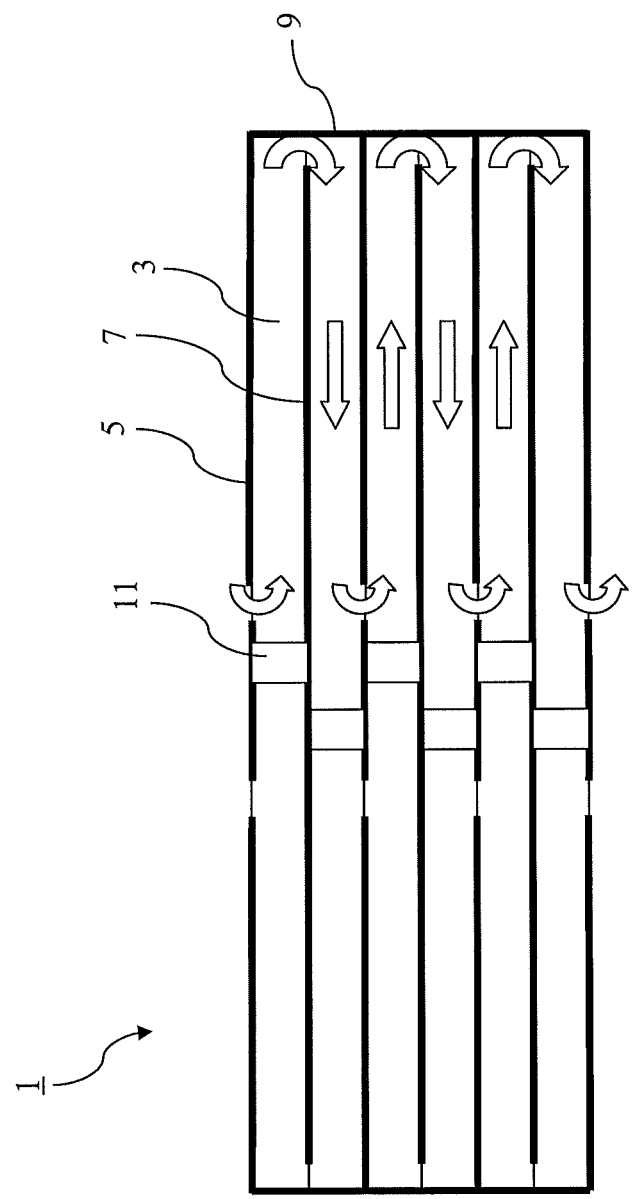
FIG. 1A is a schematic longitudinal sectional illustration of a first embodiment of the present invention.
Figure 1B:
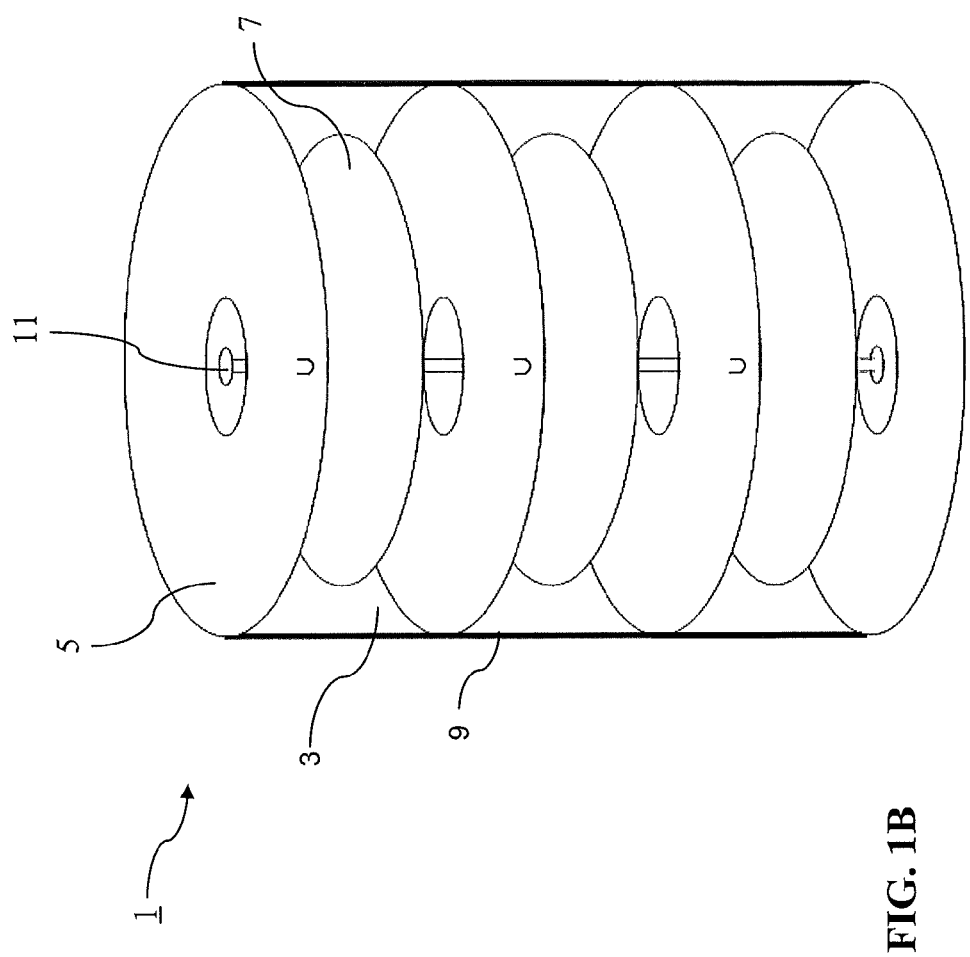
FIG. 1B is a schematic perspective illustration of a first embodiment of the present invention.

FIGS. 1A and 1B are schematic illustrations of the mechanism of action and the basic structure of a feedthrough 1, which is composed substantially solely of a liquid crystal polymer ("LCP") 3 having first and second metal layers 5 and 7 that are applied to the outside or incorporated therein. One each of the first metal layers 5 is disposed on the two faces of the substantially cylindrical feedthrough 1, and in the embodiment illustrated herein, two further of the first metal layers 5 are incorporated in the feedthrough 1, parallel to the faces. The first metal layers 5 are each in contact with a conductive casing layer 9 of the feedthrough 1 and do not extend quite to the central lead (terminal lead) 11. In contrast, the second metal layers 7, which are incorporated in the feedthrough body between the first metal layers 5, are conductively connected to the terminal lead 11, but do not extend quite to the casing lead 9.

As the arrows in FIG. 1A symbolize, in this way a labyrinth-like structure of the LCP 3 main body having considerably longer diffusion paths and reduced diffusion cross-sections is created.

The structure according to FIGS. 1A and 1B comprising the alternating connected metal layers 5 and 7 forms a capacitor with the two connections implemented by way of the conductive casing 9 and the inner conductor (terminal lead) 11, the capacitance of which can be adjusted by suitable dimensioning to a value which enables an additional function in interaction with a functional unit that is provided in the electronic device, such as, for example, a filtration of exterior electromagnetic interference by way of a suitable matched filter.

Figure 2:
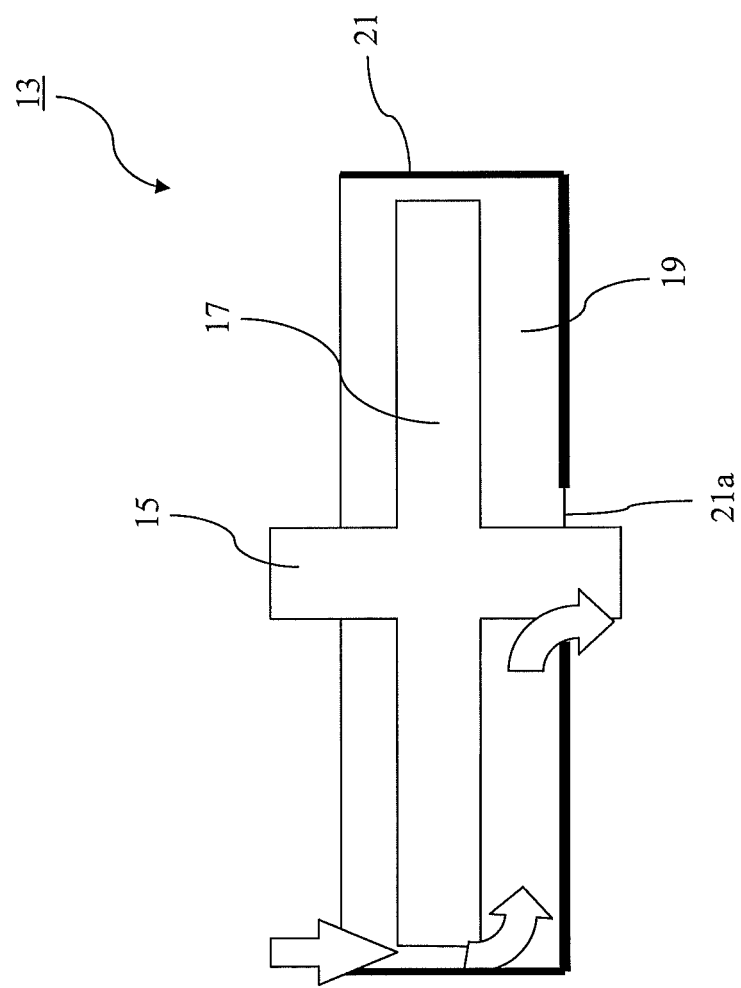
FIG. 2 is a schematic longitudinal sectional illustration of a second embodiment of the present invention.

A similar effect, albeit less pronounced, is achieved with the simplified structure of a further feedthrough 13 according to FIG. 2. A metal disk 17 is disposed around a central conductor (terminal lead) 15 and in electric contact therewith, the disk 17 being insert-molded with a liquid crystal polymer 19 such that the faces and the circumference of the disk 17 are completely enclosed in the polymer 19. The part obtained in this way is inserted in a crucible 21 made of conductive material having a central opening 21a, the diameter of which is larger than that of the terminal lead 15. In this way, electrical insulation is ensured between the terminal lead 15 and the crucible 21, and compared, for example, to a feedthrough structure without the disk 17, an extended diffusion path and reduced diffusion cross-section are achieved for diffusing ions, again indicated with arrows.

Figure 3:
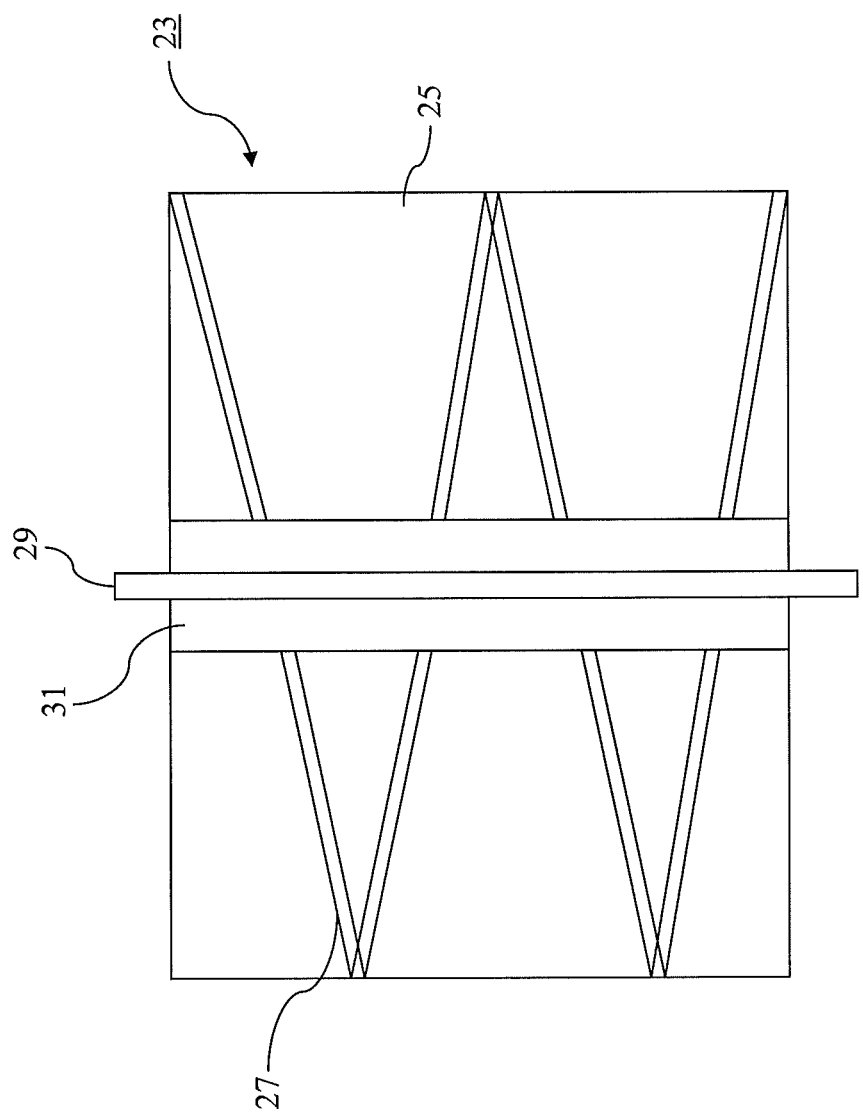
FIG. 3 is a schematic longitudinal sectional illustration of a third embodiment of the present invention.

FIG. 3 is a schematic illustration of a further possible structure using the example of a feedthrough 23 in which a spirally disposed metal foil 27 is embedded into a cylindrical main body 25 made of a liquid crystal polymer. A terminal lead 29 having a ceramic sleeve 31 is located in a central opening of said feedthrough 23 body. The feedthrough 23 is therefore a feedthrough structure that is made of both LCP and ceramic, and is thus a hybrid in terms of materials.

The implementation of the invention is not limited to the examples described above and aspects emphasized, but is likewise possible in numerous modifications, which are within the scope of standard practice in the art.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

What is claimed is:

1. An electronic device, comprising:
   a housing;
   a functional unit disposed in the housing;
   a terminal lead electrically connecting the functional unit to an outside of the housing; and
   a sealed feedthrough in the housing, the feedthrough surrounding the terminal lead and insulating it with respect to the housing, wherein the feedthrough is produced from a liquid crystal polymer,
   wherein the feedthrough is produced substantially solely from the liquid crystal polymer.

2. The electric device according to claim 1, wherein the electronic device is configured as an implantable medical electronic device.

3. The electronic device according to claim 2, wherein the electronic device is configured as a cardiac stimulator device.

4. The electronic device according to claim 3, wherein the cardiac stimulator device comprises a pacemaker or cardioverter.

5. The electronic device according to claim 1, wherein metallic elements are incorporated or applied to the liquid crystal polymer.

6. The electronic device according to claim 5, wherein the feedthrough comprises alternating metal layers which start at the circumference and a center region, respectively, and do not fully extend to the center and the circumference, respectively, and which are disposed on the faces of the feedthrough or embedded in the liquid crystal polymer inside the feedthrough and form a labyrinth structure in the longitudinal section of the housing, whereby an elongated diffusion path and reduced diffusion cross-section for molecules or ions from the inside of the electronic device to the outside is determined.

7. The electronic device according to claim 5, wherein the feedthrough comprises a metal layer extending in a spiral shape from close to an upper face to close to a lower face of the housing, which determines an elongated diffusion path and a reduced diffusion cross-section for molecules or ions from the inside of the electronic device to the outside.

8. The electronic device according to claim 5, wherein the metallic elements, together with sections of the liquid crystal polymer, form a capacitor which is arranged and connected to the functional unit of the electronic device such that in this way an electrical function of the electronic device is implemented.

9. The electronic device according to claim 8, wherein the electrical function comprises a filtration function.

10. The electronic device according to claim 5, wherein a plurality of metal layers of a labyrinth structure are rigidly connected to the terminal lead or integral therewith.

11. An electrical component, comprising:
    a housing;
    a functional unit disposed in the housing;
    a terminal lead electrically connecting the functional unit to an outside of the housing; and
    a sealed feedthrough in the housing, the feedthrough surrounding the terminal lead and insulating it with respect to the housing, wherein the feedthrough is produced from a liquid crystal polymer,
    wherein a plurality of metal layers of a labyrinth structure are rigidly connected to the terminal lead or integral therewith.

12. The electrical component according to claim 11, wherein the electrical component is configured as a capacitor.

13. The electrical component according to claim 12, wherein the capacitor comprises an electrolytic capacitor.

14. The electrical component according to claim 11, wherein the electrical component is configured as an assembly of a message transmission or filtration system.

15. An electrical component, comprising:
    a housing;
    a functional unit disposed in the housing;
    a terminal lead electrically connecting the functional unit to an outside of the housing; and
    a sealed feedthrough in the housing, the feedthrough surrounding the terminal lead and insulating it with respect to the housing, wherein the feedthrough is produced from a liquid crystal polymer,
    wherein the feedthrough is produced substantially solely from the liquid crystal polymer.

16. The electrical component according to claim 15, wherein metallic elements are incorporated or applied to the liquid crystal polymer.

17. The electrical component according to claim 16, wherein the feedthrough comprises alternating metal layers which start at the circumference and a center region, respectively, and do not fully extend to the center and the circumference, respectively, and which are disposed on the faces of the feedthrough or embedded in the liquid crystal polymer inside the feedthrough and form a labyrinth structure in the longitudinal section of the housing, whereby an elongated diffusion path and a reduced diffusion cross-section for molecules or ions from the inside of the electrical component to the outside is determined.

18. An electrical component, comprising:
    a housing;
    a functional unit disposed in the housing;
    a terminal lead electrically connecting the functional unit to an outside of the housing; and
    a sealed feedthrough in the housing, the feedthrough surrounding the terminal lead and insulating it with respect to the housing, wherein the feedthrough is produced from a liquid crystal polymer,
    wherein the electrical component is configured as an assembly of a message transmission or filtration system,
    wherein the feedthrough comprises a metal layer extending in a spiral shape from close to an upper face to close to a lower face of the housing, which determines an elongated diffusion path and a reduced diffusion cross-section for molecules or ions from the inside of the electrical component to the outside.

19. The electrical component according to claim 18, wherein the electrical component is configured as an implantable medical electronic device.

20. The electrical component according to claim 19, wherein the implantable medical electronic device is configured as a cardiac stimulator device.

* * * * *